(12) United States Patent
Fourkas et al.

(10) Patent No.: US 9,066,712 B2
(45) Date of Patent: Jun. 30, 2015

(54) INTEGRATED CRYOSURGICAL SYSTEM WITH REFRIGERANT AND ELECTRICAL POWER SOURCE

(75) Inventors: Michael Fourkas, Sunnyvale, CA (US); Ronald Williams, Menlo Park, CA (US); Punit Govenji, Los Altos Hills, CA (US); Byron Reynolds, Gilroy, CA (US)

(73) Assignee: MyoScience, Inc., Redwood City, CA (US)

( * ) Notice: Subject to any disclaimer, the term of this patent is extended or adjusted under 35 U.S.C. 154(b) by 962 days.

(21) Appl. No.: 13/255,102

(22) PCT Filed: Dec. 22, 2009

(86) PCT No.: PCT/US2009/069282
§ 371 (c)(1),
(2), (4) Date: Jul. 2, 2012

(87) PCT Pub. No.: WO2010/075438
PCT Pub. Date: Jul. 1, 2010

(65) Prior Publication Data
US 2012/0265278 A1  Oct. 18, 2012

Related U.S. Application Data

(60) Provisional application No. 61/139,837, filed on Dec. 22, 2008.

(51) Int. Cl.
*A61B 18/18* (2006.01)
*A61B 18/02* (2006.01)
(Continued)

(52) U.S. Cl.
CPC ....... *A61B 18/02* (2013.01); *A61B 2018/00041* (2013.01); *A61B 2018/0281* (2013.01); *A61B 2018/0293* (2013.01); *A61F 2007/0052* (2013.01); *A61F 2007/0056* (2013.01)

(58) Field of Classification Search
CPC ........... A61F 7/00; A61F 7/0085; A61F 7/12; A61F 2007/00; A61F 2007/0001; A61F 2007/0052; A61F 2007/0059; A61F 2007/006; A61F 2007/0063; A61F 2007/0064; A61F 2007/0068; A61F 2007/0077; A61F 2007/0078
USPC .......................................................... 606/21
See application file for complete search history.

(56) References Cited

U.S. PATENT DOCUMENTS 2,319,542 A   5/1943   Hall
2,672,032 A   3/1964   Towse
(Continued)

FOREIGN PATENT DOCUMENTS

CA   2643474 A1   9/2007
EP   0043447 A2   6/1981
(Continued)

OTHER PUBLICATIONS

The International Search Report, dated Mar. 3, 2010, for International Application No. PCT/US2009/069282, 3 pages.
(Continued)

*Primary Examiner* — Robert N Wieland
(74) *Attorney, Agent, or Firm* — Kilpatrick Townsend & Stockton LLP

(57) ABSTRACT

A system for treating tissue in a patient includes a body having a cooling fluid supply path and a tissue piercing probe in fluid communication with the cooling fluid supply path. The probe extends distally from the body and is insertable into the tissue through the patient's skin. A cooling fluid source is fluidly coupled with the probe such that when cooling is initiated, cooling fluid flows in the probe thereby cooling the probe and any adjacent tissue. A heater element is in thermal engagement with the cooling fluid source and a power source provides power to the heater element thereby heating the cooling fluid. The power source has sufficient power to heat the cooling fluid to at least a desired temperature but has insufficient power to heat the cooling fluid above a critical temperature which results in rupture of the cooling fluid source.

43 Claims, 5 Drawing Sheets

(51) Int. Cl.
*A61B 18/00* (2006.01)
*A61F 7/00* (2006.01)

(56) References Cited

U.S. PATENT DOCUMENTS

| | | |
|---|---|---|
| 3,266,492 A | 8/1966 | Steinberg |
| 3,289,424 A | 12/1966 | Lee |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A | 8/1990 | Merry |
| 5,059,197 A | 10/1991 | Urie et al. |
| 5,200,170 A | 4/1993 | McDow |
| 5,294,325 A | 3/1994 | Liu |
| 5,334,181 A | 8/1994 | Rubinsky et al. |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,814,040 A | 9/1998 | Nelson et al. |
| 5,860,970 A | 1/1999 | Goddard et al. |
| 5,879,378 A | 3/1999 | Usui |
| 5,899,897 A | 5/1999 | Rabin et al. |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 | 2/2001 | Dobak, III |
| 6,196,839 B1 | 3/2001 | Ross |
| 6,238,386 B1 | 5/2001 | Muller et al. |
| 6,277,099 B1 | 8/2001 | Strowe et al. |
| 6,277,116 B1 | 8/2001 | Utely et al. |
| 6,363,730 B1 | 4/2002 | Thomas |
| 6,371,943 B1 | 4/2002 | Racz et al. |
| 6,432,102 B2 | 8/2002 | Joye et al. |
| 6,494,844 B1 | 12/2002 | Van Bladel et al. |
| 6,503,246 B1 | 1/2003 | Har-Shai et al. |
| 6,506,796 B1 | 1/2003 | Fesus et al. |
| 6,546,935 B2 | 4/2003 | Hooven |
| 6,551,309 B1 | 4/2003 | LePivert |
| 6,562,030 B1 | 5/2003 | Abboud et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,902,554 B2 | 6/2005 | Huttner |
| 6,905,492 B2 | 6/2005 | Zvuloni et al. |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,195,616 B2 | 3/2007 | Diller et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 | 8/2009 | Bleich et al. |
| 7,641,679 B2 | 1/2010 | Joye et al. |
| 7,713,266 B2 | 5/2010 | Elkins et al. |
| 7,803,154 B2 | 9/2010 | Toubia et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,715,275 B2 | 5/2014 | Burger et al. |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0181896 A1 | 9/2003 | Zvuloni et al. |
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |

(56) References Cited

U.S. PATENT DOCUMENTS

| | | |
|---|---|---|
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173447 A1 | 8/2006 | Jay |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171334 A1 | 7/2009 | Elkins et al. |
| 2009/0221986 A1* | 9/2009 | Wang et al. .................. 604/503 |
| 2009/0248001 A1 | 10/2009 | Burger et al. |
| 2009/0264876 A1 | 10/2009 | Roy et al. |
| 2009/0299357 A1 | 12/2009 | Zhou |
| 2010/0198207 A1 | 8/2010 | Elkins et al. |
| 2011/0144631 A1 | 6/2011 | Elkins et al. |
| 2012/0065629 A1 | 3/2012 | Elkins et al. |
| 2012/0089211 A1 | 4/2012 | Curtis et al. |
| 2013/0324990 A1 | 12/2013 | Burger et al. |
| 2014/0249519 A1 | 9/2014 | Burger et al. |

FOREIGN PATENT DOCUMENTS

| | | |
|---|---|---|
| EP | 0777123 A1 | 6/1997 |
| EP | 0955012 A1 | 10/1999 |
| EP | 1074273 A1 | 2/2001 |
| EP | 1377327 B1 | 9/2007 |
| EP | 1862125 A2 | 12/2007 |
| GB | 1360353 B | 7/1974 |
| GB | 1402632 A | 8/1975 |
| JP | 60-013111 | 1/1985 |
| JP | H04-357945 A | 12/1992 |
| JP | 05-038347 A | 1/1998 |
| JP | 10-014656 A | 1/1998 |
| JP | 2001-178737 A | 7/2001 |
| JP | 2002/102268 A | 4/2002 |
| JP | 2004-511274 A | 4/2004 |
| JP | 2005-080988 A | 3/2005 |
| JP | 2006-130055 A | 5/2006 |
| JP | 2006-517118 A1 | 7/2006 |
| JP | 2008-515469 a | 5/2008 |
| RU | 2254060 | 6/2005 |
| WO | 97/49344 A1 | 12/1997 |
| WO | 01/97702 A1 | 12/2001 |
| WO | 02/092153 A2 | 11/2002 |
| WO | 2004/039440 A1 | 5/2004 |
| WO | 2004/045434 A2 | 6/2004 |
| WO | 2004/089460 A2 | 10/2004 |
| WO | 2005/000106 A2 | 1/2005 |
| WO | 2005/079321 A2 | 9/2005 |
| WO | 2005/096979 A1 | 10/2005 |
| WO | 2006/012128 A2 | 2/2006 |
| WO | 2006/023348 A1 | 3/2006 |
| WO | WO 2006/044727 A2 | 4/2006 |
| WO | 2006/062788 A2 | 6/2006 |
| WO | 2006/125835 A1 | 11/2006 |
| WO | 2006/127467 A2 | 11/2006 |
| WO | WO 2007/025106 A2 | 3/2007 |
| WO | 2007/037326 A1 | 4/2007 |
| WO | 2007-076123 A1 | 7/2007 |
| WO | 2007/089603 A2 | 8/2007 |
| WO | 2007/129121 A1 | 11/2007 |
| WO | 2007/135629 A1 | 11/2007 |
| WO | 2009/026471 A1 | 2/2009 |
| WO | 2010-075448 A1 | 7/2010 |

OTHER PUBLICATIONS

The International Search Report and the Written Opinion, dated Jul. 7, 2011, for International Application No. PCT/US2009/069282, 10 pages.

Singaporean Office Action issued in International Patent Application No. 201104541-6, dated May 13, 2013, 15 pages.

The International Search Report and the Written Opinion, dated Mar. 30, 2010, for International Application No. PCT/US2009/069304, 11 pages.

European Office Action issued in International Patent Application No. 09835799.9-2305, dated Apr. 24, 2012, 32 pages.

Singaporean Office Action issued in International Patent Application No. 201104540-8, dated Oct. 2, 2012, 8 pages.

Singaporean Examination Report issued in International Patent Application No. 201104540-8, dated May 27, 2013, 6 pages.

The International Search Report, dated Apr. 19, 2013, for International Application No. PCT PCT/US2013/021488, 12 pages.

Australian Office Action issued in International Patent Application No. 2009330012, dated Aug. 8, 2013, 3 pages.

Japanese Notice of Reasons for Rejection issued on Oct. 21, 2013 for Japanese Patent Application No. 2011-542582, with English translation, 4 pages.

European Decision to Grant issued on Jul. 18, 2013 for European Patent Application No. 09835792.4, 2 pages.

Extended European Search Report mailed on Apr. 26, 2012 for European Patent Application No. 09835792.4, 9 pages.

Japanese Notice of Reasons for Rejection issued on Oct. 7, 2013 for Japanese Patent Application No. 2011-542579, with English translation, 7 pages.

Patent Examination Report issued on Nov. 4, 2013 for Australian Patent Application No. 2009330022, 3 pages.

Examination Report issued Feb. 12, 2013 for European Patent Application No. 09835799.9, 6 pages.

Advanced Cosmetic Intervention, Inc. [webpage], retrieved from the Internet: http://www.acisurgery.com, copyright 2007, 1 page.

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

(56) References Cited

OTHER PUBLICATIONS

Cryosurgical Concepts, Inc., [webpage] "CryoProbenr™", retrieved from the Internet: <<http://www.cryo-surgical.com//>> on Feb. 8, 2008, 2 pages total.

Dasiou-Plankida, "Fat injections for facial rejuvenation: 17 years experience in 1720 patients," Journal of Cosmetic Dermatology, Oct. 22, 2004; 2(3-4): 119-125.

Foster et al., "Radiofrequency Ablation of Facial Nerve Branches Controlling Glabellar Frowning", Dermatol Surg. Dec. 2009; 35(12):1908-1917.

Har-Shai et al., "Effect of skin surface temperature on skin pigmentation during contact and intralesional cryosurgery of hypertrophic scars and Kleoids," Journal of the European Academy of Dermatology and Venereology, Feb. 2007, vol. 21, issue 2, pp. 191-198.

Magalov et al., "Isothermal vol. contours generated in a freezing gel by embedded cryo-needles with applications to cryo-surgery," Cryobiology Oct. 2007, 55(2):127-137.

Metrum CryoFlex, Cryoablation in pain management brochure, 2012, 5 pages.

Metrum CryoFlex, Cryosurgery probes and accessories catalogue, 2009, 25 pages.

One Med Group, LLC., [webpage] "CryoProbe™", retrieved from the Internet: <<http://www.onemedgroup.com/>> on Feb. 4, 2008, 2 pages total.

Rewcastle et al., "A model for the time dependent three-dimensional thermal distribution within iceballs surrounding multiple cryoprobes," Med Phys. Jun. 2001; 28(6):1125-1137.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

Utley et al., "Radiofrequency Ablation of the Nerve to the Corrugator Muscle for the Elimination of Glabellar Furrowing," Arch. Facial Plastic Surgery 1:46-48, 1999.

Yang et al., "Apoptosis induced by cryo-injury in human colorectal cancer cells is associated with mitochondrial dysfunction.," International Journal of Cancer, 2002, vol. 103, No. 3, pp. 360-369.

U.S. Appl. No. 60/987,992, filed Nov. 14, 2007, titled "Pain Management Using Cryogenic Remodeling" by Keith Burger et al.

U.S. Appl. No. 61/116,050, filed Nov. 19, 2008, titled "Cryosurgical Safety Valve Arrangement and Methods for Its Use in Cosmetic and Other Treatment" by Timothy Holland et al.

International Preliminary Report on Patentability mailed Jul. 7, 2011, for PCT Application No. PCT/US2009/069304, 8 pages.

* cited by examiner

INTEGRATED CRYOSURGICAL SYSTEM WITH REFRIGERANT AND ELECTRICAL POWER SOURCE

CROSS-REFERENCES TO RELATED APPLICATIONS

This application is a National Stage of International Application No. PCT/US2009/069282, filed Dec. 22, 2009, and which claims the benefit of U.S. Provisional Application No. 61/139,837, filed Dec. 22, 2008, the disclosures of which are incorporated herein by reference.

BACKGROUND OF THE INVENTION

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. Other embodiments may find use for a wide range of medical indications. The remodeling of the target tissue may achieve a desired change in its behavior or composition.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary enervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, improved medical devices, systems, and methods utilizing a cryogenic approach to treating the tissue have been proposed, particularly for treatment of wrinkles, fat, cellulite, and other cosmetic defects. These new techniques can provide an alternative visual appearance improvement mechanism which may replace and/or compliment known bioactive and other cosmetic therapies, ideally allowing patients to decrease or eliminate the injection of toxins and harmful cocktails while providing similar or improved cosmetic results. These new techniques are also promising because they may be performed percutaneously using only local or no anesthetic with minimal or no cutting of the skin, no need for suturing or other closure methods, no extensive bandaging, and limited or no bruising or other factors contributing to extended recovery or patient "down time." Additionally, cryogenic treatments are also desirable since they may be used in the treatment of other cosmetic and/or dermatological conditions (and potentially other target tissues), particularly where the treatments may be provided with greater accuracy and control, less collateral tissue injury and/or pain, and greater ease of use.

While these new cryogenic treatments are promising, the use of cryogenic fluids can be dangerous to the operator as well as the patient. Cryogenic fluids are often stored in a heater canister. Excessive heating of the canister could result in canister rupture and undesired fluid leakage. Additionally, many of these cryogenic systems are powered with electrical energy. A short circuit or other electrical failure could also result in unwanted canister heating and rupture. Rupture of the canister could result in dangerous projectiles flying through the air as well as cooling fluid leaking from the device and causing injury or unwanted results to the patient and/or physician. Therefore it would be desirable to provide cryogenic treatment devices and methods with additional safety features that can more carefully control storage and heating of the cryogenic fluid in the device. It would also be desirable if these safety features were also cost effective, easy to manufacture and operate.

BRIEF SUMMARY OF THE INVENTION

The present invention is generally directed to medical devices, systems and methods for cooling-induced remodeling of tissues. More specifically, the present invention relates to methods and apparatus used to facilitate safe storage of cryogenic cooling fluids.

In a first aspect of the present invention, a system for treating target tissue in a patient comprises a body having at least one cooling refrigerant supply path and at least one probe having a proximal portion, a distal tissue piercing portion and a lumen therebetween that is in fluid communication with the cooling refrigerant supply path. The at least one probe extends distally from the body and is inserted into the target tissue through the skin surface of a patient. The system also includes a refrigerant source that is fluidly coupled with the lumen such that when cooling is initiated, a refrigerant, such as a cooling fluid or gas flows in the lumen thereby cooling the probe and any adjacent target tissue. A heater element is in thermal engagement with the refrigerant source and a power source is adapted to provide power to the heater element thereby heating the refrigerant. The power source has sufficient power to heat the refrigerant to a desired temperature and the power source has insufficient power to heat the refrigerant, which may be a cooling fluid, above a critical temperature which results in rupture of the cooling fluid source.

The body may further comprise a quick disconnect mechanism disposed near a distal end thereof and that is adapted to releasably hold the at least one probe. The quick disconnect mechanism may comprise a check valve that is adapted to prevent refrigerant from flowing along the refrigerant supply path after the probe is disconnected from the body. The probe may be releasably connected with the body and may also comprise a needle having a distal end adapted to pierce tissue. The distal end of the needle may be sealed so as to prevent refrigerant from flowing therethrough.

The refrigerant, which may be a cooling fluid source, may comprise a canister that contains the refrigerant and the canister may comprise from about 1 gram to about 35 grams of nitrous oxide. The power source may comprise a disposable or rechargeable and reusable battery such as a nickel metal hydride or lithium ion battery. In some embodiments, the battery provides electrical energy at less than about 5 volts and has a capacity of 350 milliamp-hours of current or less. The critical temperature may be less than about 80% of the canister burst temperature and the desired temperature may be 30° C. The power source may comprise an alternating current power source external to the body and tethered thereto. A thermal fuse may be electrically disposed between the power source and the heater.

The system may further comprise a valve that is adapted to regulate flow of refrigerant from the canister to the lumen. In some embodiments, the system may comprise a motor that is operatively coupled with the valve such that actuation of the motor actuates the valve. The system may also comprise a controller that is electrically coupled with the power source. The controller may comprise instructions that, if executed, result in refrigerant flow from the refrigerant source to the lumen. The valve may also be manually actuated.

In a second aspect of the present invention, a method for treating target tissue in a patient comprises the steps of providing a cryogenic device having a body with a cooling refrigerant or fluid supply path, a cooling fluid source and a probe coupled with a distal region of the body. The probe has a lumen and the device also includes a heater element in thermal engagement with the cooling fluid source and a power source. The method also comprises heating the cooling fluid source with the heater wherein the power source provides power to the heater. The power source has sufficient power to heat the cooling fluid to a desired temperature but the power source has insufficient power to heat the cooling fluid above a critical temperature which results in rupture of the cooling fluid source. The probe is engaged with the target tissue and cooling the probe cools the target tissue so as to remodel the target tissue.

The probe may comprise a needle and the step of engaging the probe may comprise piercing a skin surface with the needle into the target tissue. The target tissue may comprise skin, nerve, fat, connective tissue, blood vessels, muscle, or a combination thereof. The step of cooling comprises cooling the target tissue to at least at least 0° C. and may cause physical, physiological, or structural changes therein. Cooling may include evaporating at least some of the cooling fluid from a liquid to a gas within a distal portion of the probe. The cooling refrigerant or fluid may comprise nitrous oxide, carbon dioxide, or other refrigerants.

The cryogenic device may comprise a valve and the method may further comprise the step of actuating the valve so as to regulate flow of cooling fluid from the cooling fluid source to the lumen. The cryogenic device may comprise a motor operably coupled with the valve and the method may further comprise the step of actuating the motor so as to actuate the valve. Sometimes the power source may comprise a first battery and the method may further comprise the steps of decoupling the first battery from the cryogenic device when the first battery is substantially discharged and coupling a second battery with the cryogenic device. The second battery may be at least partially charged. When the power source comprises a battery, the method may also include recharging the battery after it has been substantially discharged. Sometimes the method may also include the step of disconnecting the probe from the body and discarding the probe.

In still another aspect of the present invention, a system for cooling a target tissue in a single patient comprises a probe having a proximal portion, a distal target tissue engaging portion, and a cooling fluid supply lumen therebetween. The probe is insertable distally into the target tissue and a cooling fluid source contains a quantity of cooling fluid. A heater element is thermally engaged with the cooling fluid source and a disposable or rechargeable battery is adapted to provide power to the heater element so as to heat the cooling fluid. The power source has sufficient power to heat the cooling fluid to a desired temperature but has insufficient power to heat the cooling fluid above a critical temperature which results in rupture of the cooling fluid source. The battery also has sufficient power to operate the cryogenic device to cool the target tissue adjacent a plurality of insertion sites so as to remodel the target tissue and cosmetically enhance an appearance of the patient. The cooling fluid source may comprise a single-use canister having from about 1 gram to about 35 grams of nitrous oxide or other refrigerant and the battery may have a capacity of less than 350 milliamp-hours of current.

These and other embodiments are described in further detail in the following description related to the appended drawing figures.

DETAILED DESCRIPTION OF THE INVENTION

Figure 1A:
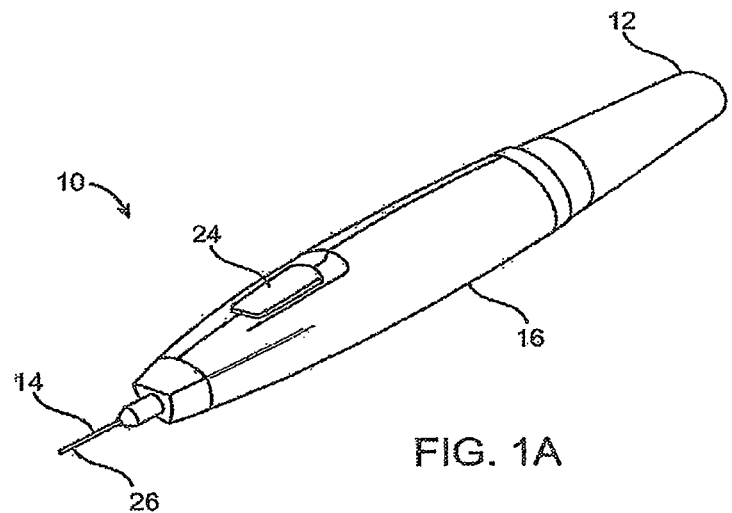
FIG. 1A is a perspective view of a self-contained subdermal cryogenic remodeling probe and system, according to an embodiment of the invention.

The present invention provides improved medical devices, systems, and methods. Embodiments of the invention will facilitate remodeling of tissues disposed at and below the skin, optionally to treat a cosmetic defect, a lesion, a disease state, and/or so as to alter a shape of the overlying skin surface.

Among the most immediate applications of the present invention may be the amelioration of lines and wrinkles, particularly by inhibiting muscular contractions which are associated with these cosmetic defects so as to improve an appearance of the patient. Rather than relying entirely on a pharmacological toxin or the like to disable muscles so as to induce temporary paralysis, many embodiments of the invention will at least in part employ cold to interrupt, modulate, or change nerve and muscle functions. Advantageously the function of, nerves, muscles, and associated tissues may be temporarily interrupted, modulated, or changed using moderately cold temperatures of 10° C. to −5° C. without permanently disabling the tissue function or structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by treating the target tissue zone and/or inducing apoptosis at temperatures from about −5° C. to about −100° C. In some embodiments, apoptosis may be induced using treatment temperatures from about −1° C. to about −15° C., or from about −1° C. to about −19° C., optionally so as to provide a longer term or permanent treatment that limits or avoids inflammation and mobilization of skeletal muscle satellite repair cells. Hence, the duration of the treatment efficacy of such subdermal cryogenic treatments may be selected and controlled, with colder temperatures, longer treatment times, and/or larger volumes or selected patterns of target tissue determining the longevity of the treatment. Using treatment temperatures colder than −5° C., tissue may be selectively modified such that cells (for example, skeletal muscle cells or nerve axons) are treated while connective tissue structures are left intact so as to ensure complete recovery or regeneration of the affected tissue, thereby providing a temporary treatment effect.

Additional description of cryogenic cooling for treatment of cosmetic and other defects may be found in U.S. Pat. No. 7,713,266, entitled "Subdermal Cryogenic Remodeling of Muscle, Nerves, Connective Tissue, and/or Adipose Tissue (Fat)," and U.S. Pat. No. 7,850,683, also entitled "Subdermal Cryogenic Remodeling of Muscles, Nerves, Connective Tissue, and/or Adipose Tissue (Fat)," the full disclosures of which are both incorporated herein by reference.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms as disclosed in copending U.S. Provisional Patent Application No. 60/987,992, filed on Nov. 14, 2007 and entitled "Pain Management Using Cryogenic Remodeling," the full disclosure of which is incorporated herein by reference.

Figure 1B:
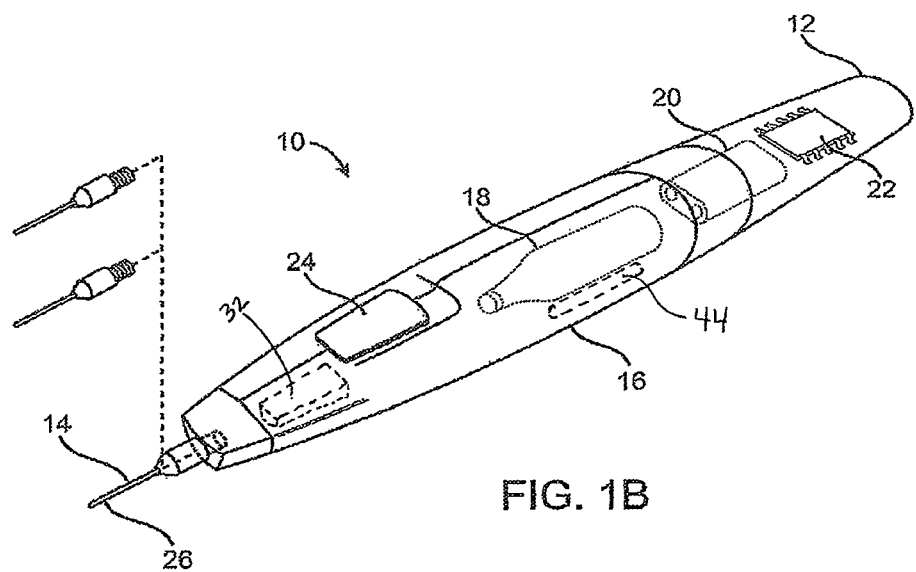
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling refrigerant supply 18, a supply valve 32 and electrical power source 20 are found within housing 16, along with a circuit 22 having a processor for controlling cooling applied by self-contained system 10 in response to actuation of an input 24. Power source 20 also supplies power to heater element 44 in order to heat the cooling refrigerant supply 18 thereby helping to create uniform coolant conditions. When actuated, supply valve 32 controls the flow of cryogenic cooling refrigerant from fluid supply 18. Some embodiments may, at least in part, be manually activated, such as through the use of a manual supply valve and/or the like, so that processors, electrical power supplies, and the like may be absent.

Extending distally from distal end 14 of housing 16 is a tissue-penetrating cryogenic cooling probe 26. Probe 26 is thermally coupled to a cooling fluid path extending from cooling refrigerant source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about 0.5 mm and 5 cm, preferably having a length from about 0.5 cm to about 1 cm (5-10 mm). Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 27, 30, or 31 gauge or smaller needle. In some embodiments, probe 26 may comprise two or more needles arranged in a linear array, such as those disclosed in U.S. Pat. No. 7,850,683, entitled "Subdermal Cryogenic Remodeling of Muscles, Nerves, Connective Tissue, and/or Adipose Tissue (Fat)," the full disclosure of which has been incorporated herein by reference. Multiple needle probe configurations allow the cryogenic treatment to be applied to a larger or more specific treatment area. Other needle configurations that facilitate controlling the depth of needle penetration and insulated needle embodiments are disclosed in U.S. Pat. No. 8,409,185, entitled "Replaceable and/or Easily Removable Needle Systems for Dermal and Transdermal Cryogenic Remodeling," the entire contents of which are incorporated herein by reference. In some embodiments needle 26 is releasably coupled with body 16 so that it may be replaced after use with a sharper needle (as indicated by the dotted line) or with a needle having a different configuration. In exemplary embodiments, the needle may be threaded into the body, it may be press fit into an aperture in the body or it may have a quick disconnect such as a detent mechanism for engaging the needle with the body. A quick disconnect with a check valve is advantageous since it permits decoupling of the needle from the body at any time without excessive coolant discharge. This can be a useful safety feature in the event that the device fails in operation (e.g. motor failure), allowing an operator to disengage the needle and device from a patient's tissue without exposing the patient to coolant as the system depressurizes. This feature is also advantageous because it allows an operator to easily exchange a dull needle with a sharp needle in the middle of a treatment. One of skill in the art will appreciate that other coupling mechanisms may be used.

Addressing some of the components within housing 16, the exemplary cooling refrigerant supply 18 comprises a canister, sometimes referred to herein as a cartridge, containing a liquid under pressure, with the liquid preferably having a boiling temperature of less than 37° C. When the refrigerant is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit the temperature, time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 and power source 20 are described below. In other embodiments, the cooling refrigerant supply 18 may comprise a canister having fins or other heat exchange elements (not illustrated) thermally coupled therewith in order to prevent overheating of the canister.

The exemplary refrigerant fluid supply 18 comprises a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures. In addition Processor 22 controls an optional security 23 means that may comprise an integrated chip having a code that requires a matching code from the disposable probe 26 to work. Also the design of the interface of probe 26 connected to the distal end of housing 14 may be a geometrical fit such that the probe 26 has a fit orientation that seats or locks into the distal end of housing 14. This prevents or minimizes the use of third party knock-off components.

Figure 1C:
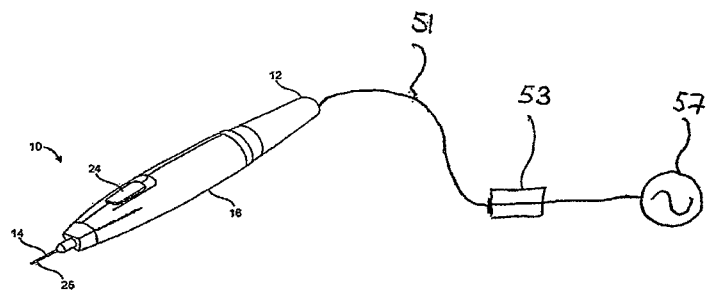
FIG. 1C is a schematic diagram of a cryogenic remodeling probe and system powered by an external power supply.
Figure 1D:
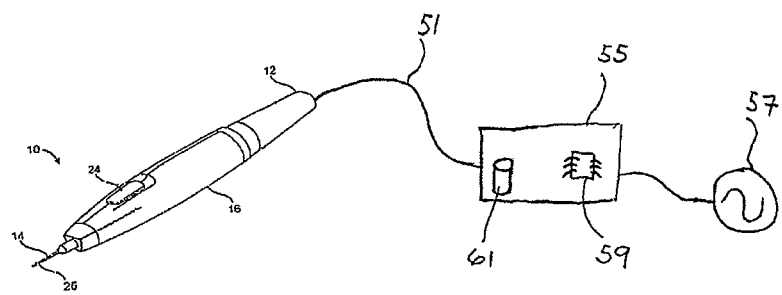
FIG. 1D is a schematic diagram of a cryogenic remodeling probe and system having a control console with a controller, and optional external power supply.
Figure 1E:
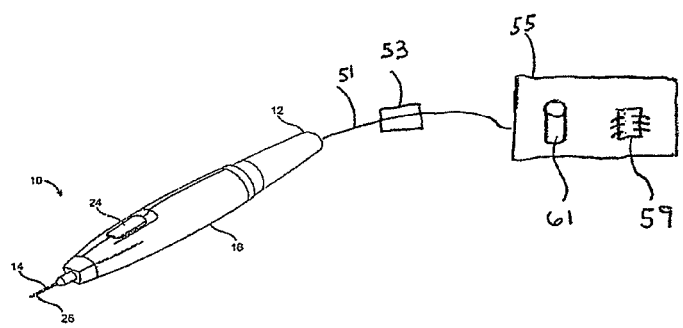
FIG. 1E is a schematic diagram of a cryogenic remodeling probe and system having a control console with an internal power supply and controller.

FIGS. 1C-1E illustrate alternative embodiments of those shown in FIGS. 1A-1B. For example, in FIG. 1C, system 10 generally takes the same form as system 10 in FIGS. 1A-1B, except that the power source has been removed from the housing, and instead a tether or power cord 51 connects the system 10 with an alternating current power supply 57 such as a wall socket. An optional fuse 53 prevents too much power from being drawn from the power supply 57, thereby preventing overheating of the refrigerant supply (not illustrated). FIG. 1D is another variation of system 10, that generally takes the same form as system 10 in FIGS. 1A-1B, with the major difference being that the power source and the controller have both been removed from the housing 16. In this embodiment, an external controller box 55 is connected with the housing 16 via a tether or cord 51, and the box 55 optionally contains either or both the controller 59 and a battery 61, which may be charged via a wall socket or other alternating current source 57. In still another variation, FIG. 1E generally takes the same form as system 10 in FIGS. 1A-1B, with the major difference being that the power source and the controller have been removed from the housing. In this embodiment, the housing 16 is coupled with an external control box 55 via a tether or cord 51. The control box 55 optionally contains either or both a battery 61 and a controller 59. A fuse 53 is electrically disposed between the control box 55 and the housing 16, to prevent too much power from being drawn from the battery 61 and overheating the refrigerant source (not illustrated).

Figure 2:
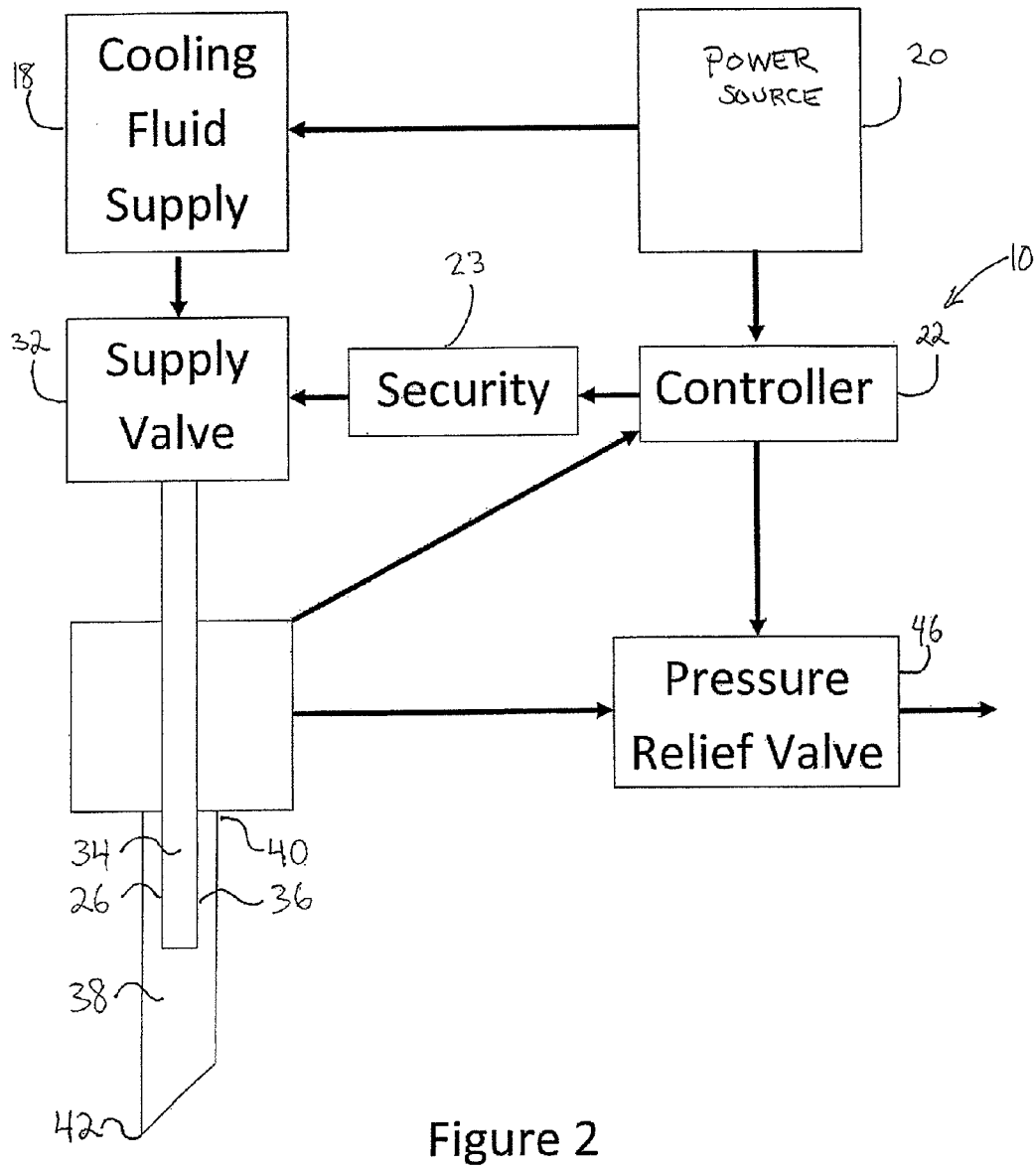
FIG. 2 schematically illustrates components that may be included in the treatment system.

Referring now to FIG. 2, the flow of cryogenic cooling fluid from fluid supply 18 is controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in U.S. Pat. No. 8,409,185, previously incorporated herein by reference.

Still referring to FIG. 2, a heater (not illustrated) heats cooling fluid supply 18 so that heated cooling fluid flows through valve 32 and through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 μm, the inner diameter often being less than about 100 μm, and typically being less than about 40 μm. Exemplary embodiments of supply tube 36 have inner lumens of between about 15 and 50 μm, such as about 30 μm. An outer diameter or size of supply tube 36 will typically be less than about 1000 μm, often being less than about 800 μm, with exemplary embodiments being between about 60 and 150 μm, such as about 90 μm or 105 μm. The tolerance of the inner lumen diameter of supply tubing 36 will preferably be relatively tight, typically being about +/−10 μm or tighter, often being +/−5 μm or tighter, and ideally being +/−3 μm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254, filed Dec. 21, 2006 and entitled "Dermal and Transdermal Cryogenic Microprobe Systems and Methods," the entire contents of which are incorporated herein by reference. U.S. Pat. No. 8,409,185, previously incorporated herein by reference, also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the tissue engaged by the needle. Controlling a pressure of the gas/liquid mixture within needle 26 substantially controls the temperature within lumen 38, and hence the treatment temperature ranges of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve allows better temperature control in the needle, minimizing transient temperatures. Further details on exhaust volume are disclosed in U.S. Pat. No. 8,409,185, previously incorporated herein by reference.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in U.S. Patent Publication No. 2008/0154,254, previously incorporated herein by reference.

The device described above relies on electrical power for the controller and actuation of the valve (if present). Additionally, in some embodiments a heater element is in thermal engagement with the canister and is used to heat the coolant to a constant desired temperature. Therefore, a suitable power source is required. The device may be powered by plugging the device into a wall socket, but in order to provide a single use handheld device, a battery is more convenient to use as the power supply. Using a battery also is advantageous because it facilitates handling of the device by a physician who does not have to worry about electrical power cords dangling from the device. While the use of a battery has advantages, it also has potential drawbacks, just as any power source would have. For example, if the battery were to short out, the resulting heat could cause overheating of the cooling fluid thereby resulting excessive pressure in the canister and subsequent canister rupture. Not only would this be dangerous because of projectiles, but this could also potentially expose the patient and/or physician to the cooling fluid resulting in unwanted results or injury. Also, if the controller or other portions of the device were to fail, the heater could be left in the "on" position similarly overheating and bursting the canister. Pressure monitoring could be implemented in such a system to prevent overheating and over pressurization of the canister, but this adds expense and complexity to the device. Therefore, it would be advantageous to provide safety features that prevent overheating and rupture of the canister which do not rely on cooling fluid pressure monitoring. A simple solution is to use a fuse in the device circuitry and thus if excessive current is drawn from the battery, the fuse will melt, breaking the power circuit. Thermal fuses may also be used such that if canister temperature exceeds a critical value, the fuse cuts power to the heater. While these features are promising, once the fuse melts, the device becomes inoperative until the fuse is replaced. Therefore, a different safety feature that prevents overheating without relying on a fuse and shutting the device down is desirable.

One embodiment of such a safety feature is to use a power source such as a battery that has sufficient capacity to power the device during a typical treatment while at the same time lacking enough power to overheat the cooling fluid canister. The battery must have enough capacity to power the controller and the heater element. In some embodiments, it is desirable to heat the cooling fluid to around 28° C. to 32° C. in order to provide uniform cooling fluid supply conditions that result in optimal probe cooling, thus the battery must have enough power to heat the canister to this desired temperature. Additionally, in embodiments where a solenoid or motor actuates the valve, the battery must also have adequate capacity to power these components as well. Using a motor instead of a battery is advantageous because the motor requires less power than a solenoid. Battery requirements and capacity may be estimated by conducting various experiments. The experiments disclosed below are exemplary only and not intended to be limiting.

Experiment 1:

Testing of the system illustrated in FIG. 1 helps determine upper limits to battery capacity. For example, a system having a 4.8 volt 350 mAh nickel metal hydride battery was used to heat an 8 gram nitrous oxide canister with a 4Ω resistive heater element and a manual valve. The battery was fully charged and allowed to continuously heat the canister for 1050 seconds until depleted. Canister temperature was monitored and it reached a maximum of 81° C. without canister rupture. Therefore, it is apparent that a 4.8 volt 350 mAh battery has insufficient capacity to heat and burst an 8 gram nitrous oxide canister and furthermore, 81° C. is not hot enough to burst this type of canister.

Experiment 2:

A 10 volt DC power supply was substituted for the battery described above in Experiment 1. Power was continuously supplied to the canister and temperature was monitored until the canister ruptured. A first canister ruptured at 161° C. and a second canister ruptured at 138° C. The second canister ruptured after 1250 seconds of heating. Therefore, the canister should not be heated above approximately 138° C. and more preferably less than a lower temperature in order to allow for some margin of safety. A larger sample size (here, n=2) is required in order to obtain a statistically significant burst temperature. Furthermore, the burst temperature may vary depending on manufacturing lot of the canister as well as based on the manufacturer. An upper burst temperature limit could be determined by testing a statistically significant number of canisters and factoring in a safety margin. In an exemplary method, the cylinder would not be heated to within 80% of its burst temperature.

A safe battery capacity that does not overheat and rupture the canister may be calculated as follows using the data generated from the two experiments described above. From Experiment 2, the power required to burst the canister is estimated according to the following.

Current delivered with 10 volt supply=10 v/4Ω, or 2.5 Amps.
Power delivered with 10 volt supply=10 v*2.5 A, or 25 Watts.
Amp hours required to burst canister=2.5 A*1250 sec/ (3600 sec per hour), or 0.868 amp-hours, or 868 milli-amp-hours.
Watt-hours required to burst canister=25 W*1250 sec/ (3600 sec per hour), or 8.68 Watt-hours.

The data from Experiment 1 confirms that the 4.8 volt 350 milliamp-hour battery would have insufficient capacity to rupture the canister. Actual battery capacity was calculated to be:

Current supplied to heater=4.8 v/4Ω, or 1.17 Amps.
Power delivered=4.8 v*1.17 Amps=5.62 Watts.
Watt hours delivered=5.62 Watts*1050 sec/(3600 sec per hour), or 1.64 Watt-hours.
Battery capacity=1050 sec/(3600 sec per hour)*1.17 Amps, or 0.341 Amp-hours, or 341 milliamp-hours.

Thus, the 4.8 volt, 350 milliamp-hour battery does not have adequate capacity to overheat the canister and is therefore intrinsically safe given the parameters described above. In order to provide a 2× safety factor, battery capacity should not exceed 4.3 Watt-hours or 430 milliamp-hours. One of skill in the art will of course appreciate that these calculations are based on a specific heater element and battery as well as other factors such as the type of canister, heater/canister interface and other system features. Any changes to the system can alter these estimates which are presented for exemplary use only.

Figure 3:
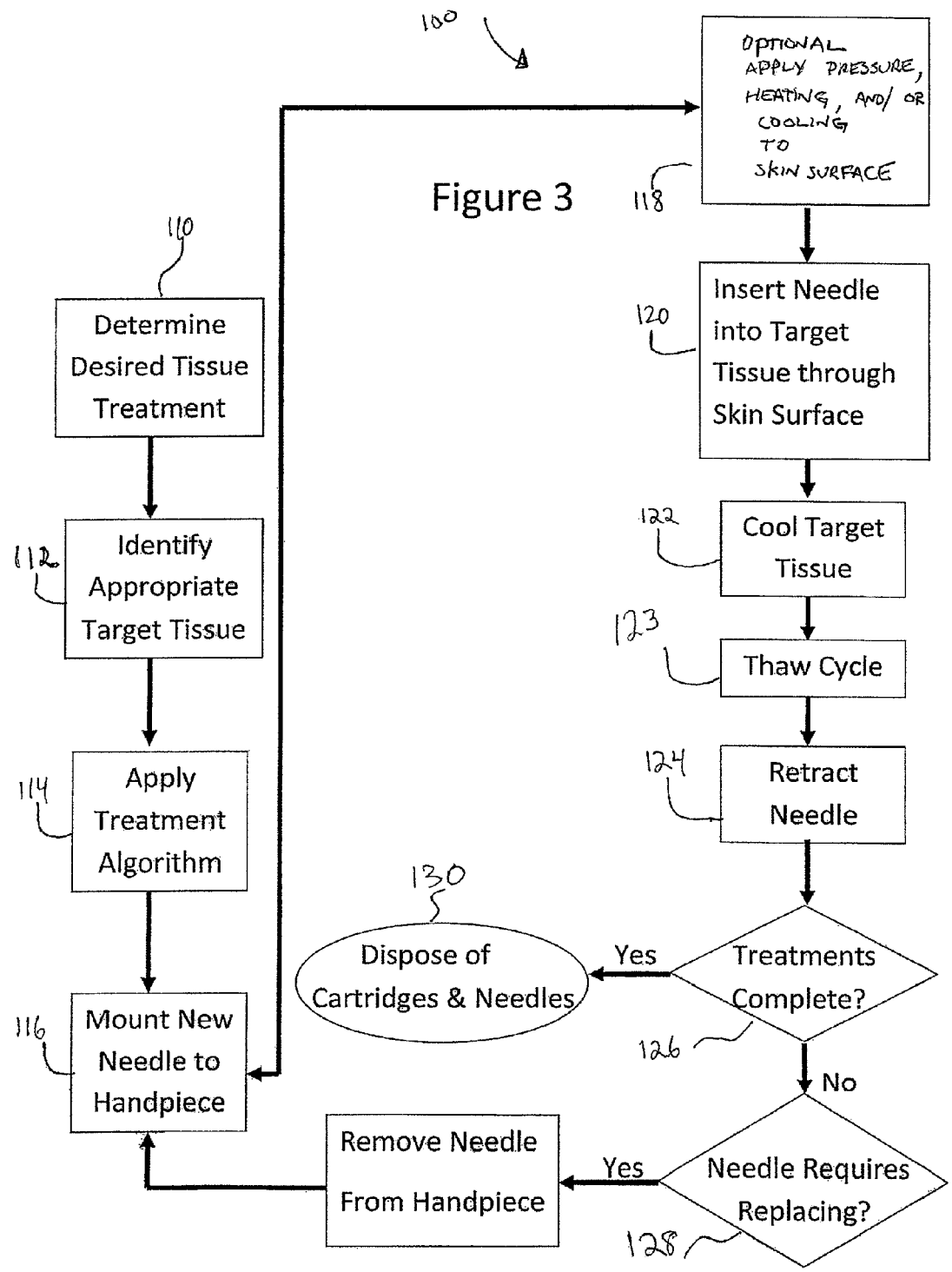
FIG. 3 is a flow chart schematically illustrating a method for treatment using the disposable cryogenic probe and system of FIG. 1B.

Referring now to FIG. 3, a method 100 facilitates treating a patient using a cryogenic cooling system having a self-contained disposable or reusable handpiece, replaceable needles such as those of FIG. 1B and a limited capacity battery. Method 100 generally begins with a determination 110 of the desired tissue therapy and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. The application of the treatment algorithm 114 may include the control of multiple parameters such as temperature, time, cycling, pulsing, and ramp rates for cooling or thawing of treatment areas. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Upon completion of the cryogenic cooling cycle the needles will need additional "thaw" time 123 to thaw from the internally created ice ball to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Figure 4:
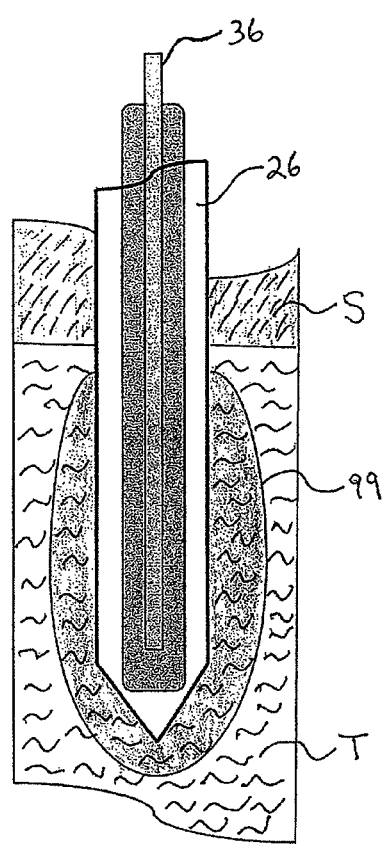
FIG. 4 illustrates the cryogenic probe of FIG. 1B inserted through a patient's skin into target tissue.

The needle can then be retracted 124 from the target tissue. If the treatment is not complete 126 and the needle does not require replacing 128, optionally pressure and/or cooling and/or heating can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded. In some cases, the power source used to provide energy to the system is a battery and this may be replaced or re-charged when depleted. FIG. 4 illustrates the needle 26 of FIGS. 1A-1B and FIG. 2 after it has pierced through a patient's skin S and into the adjacent treatment tissue T. After cryogenic cooling fluid is heated and in injected into the needle 26 via supply tube 36, a region 99 of target tissue T is cooled sufficiently to effect the desired remodeling of at least a portion of the target tissue. The cooled region 99 may be controlled and shaped to treat varying tissue volumes.

A variety of target treatment temperatures, times, and cycles may be applied to differing target tissues to as to achieve the desired remodeling. For example, (as more fully described in U.S. Pat. Nos. 7,713,266 and 7,850,683, both previously incorporated herein by reference).

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the independent claims.

What is claimed is:

1. A system for treating target tissue in a patient, said system comprising:
   a body comprising at least one cooling refrigerant supply path;
   at least one probe having a proximal portion, a distal tissue piercing portion and a lumen therebetween in fluid communication with the cooling refrigerant supply path, the at least one probe extending distally from the body and insertable into the target tissue through a skin surface of the patient;
   a refrigerant source fluidly coupled with the lumen such that when cooling is initiated, refrigerant flows in the lumen thereby cooling the probe and any adjacent target tissue;
   a heater element in thermal engagement with the refrigerant source; and
   a power source adapted to provide power to the heater element thereby heating the refrigerant source, wherein the power source has sufficient power to heat the refrigerant a desired temperature, and
   wherein the power source has insufficient power to heat the refrigerant above a critical temperature which results in rupture of the refrigerant source.

2. The system of claim 1, wherein the body further comprises a quick disconnect mechanism disposed near a distal end thereof and adapted to releasably hold the at least one probe.

3. The system of claim 2, wherein the quick disconnect mechanism comprises a check valve adapted to prevent refrigerant from flowing along the refrigerant fluid supply path after the probe is disconnected from the body.

4. The system of claim 1, wherein the at least one probe is releasably connected with the body.

5. The system of claim 1, wherein the at least one probe comprises a needle, the needle having a distal end adapted to pierce tissue.

6. The system of claim 5, wherein the distal end of the needle is sealed so as to prevent the refrigerant from flowing therethrough.

7. The system of claim 1, wherein the refrigerant source comprises a canister, the canister containing the refrigerant.

8. The system of claim 7, wherein the canister comprises from about 1 gram to about 35 grams of nitrous oxide.

9. The system of claim 1, wherein the power source comprises a disposable or reusable battery.

10. The system of claim 1, wherein the power source comprises an alternating current power source external to the body and tethered thereto, and wherein a thermal fuse is electrically disposed between the power source and the heater.

11. The system of claim 1, wherein the critical temperature is less than about 80% of canister burst temperature.

12. The system of claim 1, wherein the desired temperature is 35° C.

13. The system of claim 9, wherein the battery provides electrical energy at less than about 5 volts and has a capacity of 350 milliamp-hours of current or less.

14. The system of claim 1, wherein the power source comprises a reusable battery.

15. The system of claim 14, wherein the battery comprises a nickel metal hydride or lithium ion battery.

16. The system of claim 1, further comprising a valve adapted to regulate flow of refrigerant from the canister to the lumen.

17. The system of claim 16, further comprising a motor, the motor operatively coupled with the valve and adapted to actuate the valve.

18. The system of claim 16, wherein the valve is manually actuated.

19. The system of claim 1, further comprising a controller electrically coupled with the power source, the controller comprising instructions that, if executed, result in refrigerant flow from the cooling fluid source to the lumen.

20. A method for treating target tissue in a patient, said method comprising:
   providing a cryogenic device having a body with a cooling fluid supply path, a cooling fluid source, a probe coupled with a distal region of the body and having a lumen, a heater element in thermal engagement with the cooling fluid source and a power source;
   heating the cooling fluid source with the heater, the power source providing power to the heater, wherein the power source has sufficient power to heat the cooling fluid to at least a desired temperature and wherein the power source has insufficient power to heat the cooling fluid above a critical temperature which results in rupture of the cooling fluid source;
   engaging the probe with the target tissue; and
   cooling the target tissue with the probe so as to remodel the target tissue.

21. The method of claim 20, wherein the power source comprises a battery.

22. The method of claim 21, wherein the battery provides electrical energy at less than about 5 volts and has a capacity of 350 milliamp-hours of current or less.

23. The method of claim 20, wherein the power source comprises a nickel metal hydride battery.

24. The method of claim 20, wherein the desired temperature is 30° C.

25. The method of claim 20, wherein the critical temperature is 130° C.

26. The method of claim 20, wherein the probe comprises a needle and the step of engaging the probe comprises piercing a skin surface with the needle into the target tissue.

27. The method of claim 20, wherein the target tissue comprises skin.

28. The method of claim 20, wherein the target tissue comprises muscle.

29. The method of claim 20, wherein the step of cooling comprises cooling the target tissue to at least 0° C.

30. The method of claim 29, wherein the step of cooling of the target tissue induces necrosis therein.

31. The method of claim 20, wherein the step of cooling comprises evaporating at least some of the cooling fluid from a liquid to a gas within a distal portion of the probe.

32. The method of claim 20, wherein the cooling fluid comprises nitrous oxide.

33. The method of claim 20, wherein the cryogenic device comprises a valve and the method further comprises the step of actuating the valve so as to regulate flow of cooling fluid from the cooling fluid source to the lumen.

34. The method of claim 33, wherein the cryogenic device comprises a motor operably coupled with the valve and the method further comprises the step of actuating the motor so as to actuate the valve.

35. The method of claim 20, wherein the power source comprises a first battery and the method further comprises:
   decoupling the first battery from the cryogenic device when the first battery is substantially discharged; and
   coupling a second battery with the cryogenic device, the second battery being at least partially charged.

36. The method of claim 20, wherein the power source comprises a battery and the method further comprises:
   recharging the battery after it has been substantially discharged.

37. The method of claim 20, further comprising the step of disconnecting the probe from the body and discarding the probe.

38. A system for cooling a target tissue in a single patient, said system comprising:
   a probe having a proximal portion, a distal target tissue engaging portion, and a cooling fluid supply lumen therebetween, the probe insertable distally into the target tissue;
   a cooling fluid source containing a quantity of cooling fluid;
   a heater element thermally engaged with the cooling fluid source; and
   a battery or power source adapted to provide power to the heater element so as to heat the cooling fluid,
   wherein the power source has sufficient power to heat the cooling fluid to at least a desired temperature, and
   wherein the power source has insufficient power to heat the cooling fluid above a critical temperature which results in rupture of the cooling fluid source, and
   wherein the battery has sufficient power to operate the cryogenic device to cool the target tissue adjacent a plurality of insertion sites so as to remodel the target tissue and cosmetically enhance an appearance of the patient.

39. The system of claim 35, wherein the cooling fluid source comprises a single-use canister holding the cooling fluid.

40. The system of claim 38, wherein the battery comprises less than 450 milliamp-hours of current.

41. The system of claim 38, wherein the cooling fluid comprises from about 1 gram to about 35 grams of nitrous oxide.

42. The system of claim 38, wherein the desired temperature is 30° C.

43. The system of claim 38, wherein the critical temperature is 130° C.

* * * * *